US012258325B2

(12) United States Patent
Hagberg et al.

(10) Patent No.: US 12,258,325 B2
(45) Date of Patent: Mar. 25, 2025

(54) COLOR STABILIZATION OF MONOMERS AND OTHER REACTANTS FOR FORMING BIO-BASED POLYMERS

(71) Applicants: Archer Daniels Midland Company, Decatur, IL (US); DuPont Industrial Biosciences USA, LLC, Wilmington, DE (US)

(72) Inventors: Erik Hagberg, Decatur, IL (US); Chi Cheng Ma, Champaign, IL (US); Kenneth F. Stensrud, Decatur, IL (US)

(73) Assignees: Archer Daniels Midland Company, Decatur, IL (US); DuPont Industrial Biosciences USA, LLC, Wilmington, DE (US)

(*) Notice: Subject to any disclaimer, the term of this patent is extended or adjusted under 35 U.S.C. 154(b) by 524 days.

(21) Appl. No.: 17/252,964

(22) PCT Filed: Jun. 18, 2019

(86) PCT No.: PCT/US2019/037646
§ 371 (c)(1),
(2) Date: Dec. 16, 2020

(87) PCT Pub. No.: WO2019/246034
PCT Pub. Date: Dec. 26, 2019

(65) Prior Publication Data
US 2021/0130311 A1    May 6, 2021

Related U.S. Application Data

(60) Provisional application No. 62/686,415, filed on Jun. 18, 2018.

(51) Int. Cl.
*C07D 307/68* (2006.01)
(52) U.S. Cl.
CPC ................. *C07D 307/68* (2013.01)
(58) Field of Classification Search
CPC ...... C07D 307/68; A61K 31/341; C08K 5/14; C08G 63/66; C08G 63/78
USPC ........................................................ 549/485
See application file for complete search history.

(56) References Cited

U.S. PATENT DOCUMENTS

| 9,567,431 B2 | 2/2017 | Sipos |
| 2010/0168322 A1 | 7/2010 | Ikoshi et al. |
| 2017/0008997 A1 | 1/2017 | Honcoop et al. |

FOREIGN PATENT DOCUMENTS

| CN | 104395512 | 3/2015 |
| CN | 105007913 | 10/2015 |
| CN | 105849188 | 8/2016 |
| CN | 110234677 | 9/2019 |
| EP | 3 574 035 | 12/2019 |
| JP | H09-169643 | 6/1997 |
| JP | 2015-518093 | 6/2015 |
| JP | 2017-504684 | 2/2017 |
| JP | 2017-533320 | 11/2017 |
| KR | 10-2014-0143414 | 12/2014 |
| WO | 2013/149222 | 10/2013 |
| WO | 2014/158554 | 10/2014 |
| WO | 2015/095466 A2 | 6/2015 |
| WO | 2015/095466 A3 | 6/2015 |
| WO | 2015095466 | 6/2015 |
| WO | 2015137806 | 9/2015 |
| WO | 2015142181 | 9/2015 |
| WO | 2017/023174 | 2/2017 |
| WO | WO2017019447 A1 * | 2/2017 |
| WO | 2018/139919 | 8/2018 |
| WO | 2019/060403 | 3/2019 |

OTHER PUBLICATIONS

Third-Party Observation dated Oct. 20, 2022, in European Application No. 20190823609, 3 pages.
Extended European Search Report dated Jul. 27, 2021 in European Application No. 19823609.3.
International Search Report dated Aug. 26, 2019 in PCT/US2019/037646.
Written Opinion dated Aug. 26, 2019 in PCT/US2019/037646.
First Indian Examination Report dated Apr. 7, 2022 in Indian Application No. 202017055341, with English translation, 6 pages.
Indian Hearing Notice dated Nov. 30, 2022, in Indian Application No. 202017055341, with English translation, 3 pages.
Japanese Office Action dated Jun. 27, 2023, in Japanese Patent Application No. 2020-570484, with English translation, 7 pages.
Yu et al., Synthesis, Characterization and Thermal Properties of Bio-Based Poly(Ethylene 2,5-Furan Dicarboxylate), Journal of Macromolecular Science, Part B, vol. 55, No. 12, 2016, pp. 1135-1145.
Chinese Office Action dated Mar. 2, 2023, in Chinese Application No. 201980041435.1, 9 pages.
Brazilian Search Report dated May 3, 2023, in Brazilian Application No. 112020025725-7, with English translation, 8 pages.
European Communication pursuant to Article 94(3) EPC dated Feb. 7, 2024, in European Application No. 19823609.3, 4 pages.

(Continued)

*Primary Examiner* — Taylor V Oh
(74) *Attorney, Agent, or Firm* — Grüneberg and Myers PLLC

(57) ABSTRACT

Compositions and methods are provided for the production of bio-based polymers (e.g., polymers made from glucose), including polyesters, as well as end products resulting from such production, in which one or more color stabilizing additive compounds is utilized. The additive(s) may be used in the stabilization of a monomer or prepolymer that is reacted in such production methods, prior to obtaining the polymer. Particular bio-based polymers are those having furandicarboxylate moieties or residues in their backbone structure, with poly(alkylene furan dicarboxylate) polymers, such as polyethylene furan dicarboxylate) (PEF) and poly (trimethylene furan dicarboxylate) (PTF) being representative.

14 Claims, No Drawings

(56) References Cited

OTHER PUBLICATIONS

Chinese Office Action dated Mar. 29,2024, in Chinese Application No. 201980041435.1, 7 pages.
Japanese Office action dated Mar. 12, 2024, in Japanese Application No. 2020-570484, 4 pages.
Korean Office Action dated May 29, 2024, in Korean Application No. 10-2020-7036035, with English translation, 8 pages.
Korean Office Action dated Jan. 10, 2024, issued in Korean Patent Application No. 10-2020-7036035, with English translation, 6 pages.

* cited by examiner

COLOR STABILIZATION OF MONOMERS AND OTHER REACTANTS FOR FORMING BIO-BASED POLYMERS

CROSS-REFERENCE TO RELATED APPLICATIONS

This application is the National Stage entry under § 371 of International Application No. PCT/US2019/037646, filed on Jun. 18, 2019, and which claims the benefit of U.S. Provisional Application No. 62/686,415, filed on Jun. 18, 2018. The content of each of these applications is hereby incorporated by reference in its entirety.

TECHNICAL FIELD

The present invention relates to compositions and methods for color stabilization of monomers and other reactants, used to produce bio-based polymers, including those having furandicarboxylate moieties.

BACKGROUND ART

The depletion of fossil fuels has created major incentives for seeking alternative sources to petroleum-based carbon for the synthesis of so-called "platform" molecules that can serve as the building blocks for commercially significant products. Biomass is currently viewed as a potential replacement from which many such high value chemicals can be derived, but the development of sustainable technologies for the production of such chemicals from renewable resources remains a significant challenge.

The bio-based monomers, 2,5-furandicarboxylic acid (FDCA) and its dimethyl ester derivative, 2,5-furandicarboxylic acid, dimethyl ester (FDME) are recognized as important starting materials in the production of poly(alkylene furan dicarboxylate) polymers that can substitute for their petroleum derived analogs, namely poly(alkylene terephthalate) polymers, such as polyethylene terephthalate (PET). Prominent examples of poly(alkylene furan dicarboxylate) polymers are poly(ethylene furan dicarboxylate), or PEF, and poly(trimethylene furan dicarboxylate), or PTF, in which the different polymer backbones of these polyesters are respectively obtained by reaction of FDCA or FDME with the different co-monomers of ethylene glycol and 1,3-propane diol. The bio-plastic PEF exhibits superior properties in a number of respects, relative to the petroleum derived analog PET, particularly in the area of packaging. For example, blends of PEF and PET can provide improved barrier properties with respect to $CO_2$ and $O_2$, prolonging shelf life over pure PET and providing an acceptable container for products such as beer which are susceptible to oxidative degradation. Other packaging applications of PEF include films used to manufacture pouches, wrappers, and heat shrink materials having high mechanical strength and recyclability.

In general, both FDCA and FDME are useful platform molecules in the production of polyamides, polyurethanes, and polyesters having diverse applications as plastics, fibers, coatings, adhesives, personal care products, and lubricants. A significant consideration with respect to polymers that are made from these monomers is their color and color stability, i.e., resistance to color degradation over time, particularly resulting from exposure to a combination of heat and oxygen (e.g., air). Color, or more appropriately the absence of color, is important for applications such as food packaging and particularly beverage bottle manufacturing, in which a lack of transparency or possible yellowness in the plastic are readily perceived and may be equated to an inferior product. To date, the art has proposed the addition of color stabilizing agents to poly(alkylene furan dicarboxylate) polymers, for example according to WO 2017/023174. Alternatively, particular catalyst systems in the prepolymerization and polycondensation steps used to produce these polymers are disclosed in U.S. Pat. No. 9,567,431 as having a positive impact on color generation.

In the continuing effort to establish poly(alkylene furan dicarboxylate) polymers as commercially viable alternatives to their petroleum-based counterparts, there remains an ongoing need to address undesirable color formation.

SUMMARY OF THE INVENTION

Aspects of the invention are associated with the discovery of approaches to mitigating color formation in bio-based polymers, and/or improving their color stability, through using one or more color stabilizing additive compounds in compositions comprising monomers, such as 2,5-furandicarboxylic acid (FDCA) and its dimethyl ester derivative, 2,5-furandicarboxylic acid, dimethyl ester (FDME), for synthesizing these polymers. Representative bio-based polymers therefore include those having furandicarboxylate moieties or residues in their backbone structure, with poly(alkylene furan dicarboxylate) polymers, such as poly(ethylene furan dicarboxylate) (PEF) and poly(trimethylene furan dicarboxylate) (PTF) providing specific examples of bio-based polyesters.

The development of color in monomers and/or other precursors (e.g., prepolymers) is now recognized as a significant contributing factor to undesirable color in the bio-based polymers made from such starting materials or reactants. Without being bound by theory, color in the end product can manifest as the result of a cascading or propagating effect, from the monomer through polymer synthesis, which is difficult to control once initiated.

Further aspects of the invention reside in the recognition that FDCA and FDME monomer compositions can develop color, regardless of their initial purity and/or quality, in terms of colorlessness. Even highly pure samples exhibiting no detectable color at first, can turn yellow at seventies depending on a time/temperature exposure profile, and even in environments with limited oxygen availability (e.g., in a sealed headspace environment).

Advantageously, color stabilizing additives in compositions comprising monomers or polymer precursors (e.g., prepolymers), which are reacted to produce bio-based polymers such as polyesters, can effectively hinder or even prevent unwanted color development in the polymer end product and/or otherwise improve its color stability. Such effects may be manifested, for example, in resistance to such color development upon aging in the normal service environment of a bio-based polymer, such as in a packaging application. This is particularly important in view of strict tolerances for color in industrial materials such as beverage containers, as well as the overall perception of the consumer who, being familiar with the high transparency of conventional materials such as PET, may be reluctant to accept a substitute that is perceived inferior on the basis of color. Accordingly, those skilled in the art will appreciate from the present disclosure that the compositions, methods, and articles of manufacture (including polymer blends) described herein are of important commercial consequence, in terms of their advantages for providing viable alternatives to PET and other conventional products.

These and other aspects and associated advantages, as well as a number of particular embodiments, will become apparent from the following Detailed Description.

DETAILED DESCRIPTION OF EMBODIMENTS

Embodiments of the invention relate to compositions and methods for, as well as end products resulting from, the production of bio-based polymers in which one or more color stabilizing additive compounds (or simply one or more "additives") is utilized. The additive(s) may, for example, stabilize a monomer or prepolymer used for such production, prior to obtaining the polymer. Particular bio-based polymers of interest are those having furandicarboxylate moieties or residues in their backbone structure, with poly (alkylene furan dicarboxylate) polymers, such as poly(ethylene furan dicarboxylate) (PEF) and poly(trimethylene furan dicarboxylate) (PTF) being representative. According to some embodiments, the color stabilizing additive compound(s) may remain in the polymer, for example to continue to hinder color development during its end use. In other embodiments, the color stabilizing additives compound(s) may be removed from the polymer, for example in a separation step such as extraction, during its production. In either event, however, the additive(s) beneficially improve the color (i.e., reduce the formation of color) of the polymer, by correspondingly improving the color or color stability of monomers and/or precursors used in this production.

Color stabilizing additive compounds may therefore be included in compositions comprising a monomer, e.g., 2,5-furandicarboxylic acid (FDCA) and/or an esterified derivative thereof. This can advantageously reduce the extent of color formation during periods (e.g., prolonged storage periods) between the synthesis of monomer and its use in the production of a bio-based polymer as described herein. Representative compositions therefore comprise, consist of, or consist essentially of, FDCA or an esterified derivative thereof (e.g., its methyl ester derivative, 2,5-furandicarboxylic acid, dimethyl ester (FDME)) and one or more color stabilizing additive compounds as described herein. Particular compositions comprise, consist of, or consist essentially of, FDME and one or more of such additives. Since FDCA, as well as FDME and other esterified derivatives, are solid at room temperature, such compositions may be prepared, for example, by melting the monomer of interest, dispersing the desired additive(s) uniformly into the melt, and optionally solidifying the resulting, stabilized composition (e.g., by active cooling or simply allowing the composition to return to ambient conditions). In other embodiments, the desired additive(s) may be introduced at one or more steps during production of the bio-based polymer as further elaborated below, for example, in the course of synthesizing FDCA (e.g., by oxidization of 5-hydroxymethylfurfural or a derivative thereof); producing an esterified intermediate or transesterified intermediate, either of which intermediate may be considered a prepolymer; and/or polymerizing such intermediate by polycondensation to yield the copolymer.

Representative color stabilizing additive compounds include substituted phenols, which refer to compounds having at least one phenol moiety, but possibly two or more phenol moieties, in which the benzene ring(s) of such moiety or moieties have at least one substituent, other than the hydroxyl substituent. Particular examples of such substituents are alkoxy and alkyl substituents, with methoxy and tert-butyl substituents being preferred. Therefore, examples of substituted phenols include alkoxy-substituted (e.g., methoxy-substituted) and alkyl-substituted (e.g., tert-butyl substituted) phenols, which are namely compounds having at least one phenol moiety, but possibly two or more phenol moieties, with one or more alkoxy (e.g., methoxy) and alkyl (e.g., tert-butyl) substituents, respectively. In the case of tert-butyl-substituted phenols, these compounds are often referred to as "hindered phenols," in view of the steric hindrance resulting from the geometry of these substituents.

Substituted phenols include butylated hydroxyanisole (BHA); 2,6-dimethoxyphenol (DMP); 2,6-di-tert-butyl-4-methoxylphenol (DTMP); pentaerythritol tetrakis[3-[3,5-di-tert-butyl-4-hydroxyphenyl] propionate (PETC); 2-tert-butylhydroquinone (TBHQ); ethylenebis (oxyethylene) bis-(3-(5-tert-butyl-4-hydroxy-m-tolyl)-propionate); and octadecyl-3-(3,5-di-tert-butyl-4-hydroxyphenyl)-propionate. Of these compounds, (i) BHA, DMP, and DTMP are methoxy-substituted phenols, and (ii) DTMP, PETC, TBHQ, ethylenebis (oxyethylene) bis-(3-(5-tert-butyl-4-hydroxy-m-tolyl)-propionate); and octadecyl-3-(3,5-di-tert-butyl-4-hydroxyphenyl)-propionate are tert-butyl-substituted phenols. Other color stabilizing additive compounds include phenyl-substituted amines (e.g., 4,4'-bis(α,α-dimethylbenzyl) diphenylamine (XDPA)), phosphites (e.g., tris(2,4-di-tert-butylphenyl)phosphite), and antioxidant vitamins (e.g., ascorbic acid). The compound PETC is commercially available as Irganox®1010 (BASF) or Dovernox®10 (Dover Chemical Corp.); the compound ethylenebis (oxyethylene) bis-(3-(5-tert-butyl-4-hydroxy-m-tolyl)-propionate) is commercially available as Irganox®245 (BASF); the compound tris(2,4-di-tert-butylphenyl)phosphite is commercially available as Irgafos®168 (BASF); and the compound octadecyl-3-(3,5-di-tert-butyl-4-hydroxyphenyl)-propionate is commercially available as Irganox®1076 (BASF) or Dovernox®76 (Dover Chemical Corp.).

Compositions comprising a monomer, precursor (e.g., prepolymer), or bio-based polymer as described herein may comprise a combination of color stabilizing additive compounds, including a combination of any of the compounds and/or classes of compounds as described above, such as a combination of one or more tert-butyl-substituted phenols and one or more phosphites. For example, the combination of 50 wt-% PETC and 50 wt-% tris(2,4-di-tert-butylphenyl) phosphite is commercially available as Irganox®B255 (BASF). The combination of 20 wt-% octadecyl-3-(3,5-di-tert-butyl-4-hydroxyphenyl)-propionate and 80 wt-% tris(2, 4-di-tert-butylphenyl)phosphite is commercially available as Irganox®B900 (BASF). The combination of 50 wt-% PETC and 50 wt-% tris(2,4-di-tert-butylphenyl)phosphite is commercially available as Irganox®B225 (BASF).

Color stabilizing additive compounds may be present in a monomer, precursor (e.g., prepolymer), or bio-based polymer as described herein, in an amount, or combined amount in the case of a combination, generally from 10 parts per million by weight (wt-ppm) to 1 percent by weight (wt-%), typically from 50 wt-ppm to 2000 wt-ppm, and often from 50 wt-ppm to 1500 wt-ppm. According to preferred embodiments, the additive BHA may be present in a composition (e.g., comprising FDCA to stabilize this monomer) in an amount from 100 wt-ppm to 500 wt-ppm, or the additive Irganox®245 may be present in a composition (e.g., comprising FDCA to stabilize this monomer) in an amount from 800 wt-ppm to 1200 wt-ppm.

In other preferred embodiments, the additive BHA may be present in a composition (e.g., comprising FDME to stabilize this monomer) in an amount from 50 wt-ppm to 800 wt-ppm or, more preferably, from 50 wt-ppm to 500 wt-ppm. In other preferred embodiments, the additive DMP may be present in a composition (e.g., comprising FDME to stabilize this monomer) in an amount from 200 wt-ppm to 1500 wt-ppm or, more preferably, from 400 wt-ppm to 600 wt-ppm. In other preferred embodiments, the additive DTMP may be present in a composition (e.g., comprising FDME to stabilize this monomer) in an amount from 50 wt-ppm to 100 wt-ppm. In other preferred embodiments, the additive XDPA may be present in a composition (e.g., comprising FDME to stabilize this monomer) in an amount from 100 wt-ppm to 1500 wt-ppm. In other preferred embodiments, the additive PETC may be present in a composition (e.g., comprising FDME to stabilize this monomer) in an amount from 200 wt-ppm to 1500 wt-ppm. In other preferred embodiments, the additive Irganox®245 may be present in a composition (e.g., comprising FDME to stabilize this monomer) in an amount from 50 wt-ppm to 1500 wt-ppm or, more preferably, from 50 wt-ppm to 100 wt-ppm. In other preferred embodiments, the additive Irganox®B900 may be present in a composition (e.g., comprising FDME to stabilize this monomer) in an amount from 50 wt-ppm to 1500 wt-ppm or, more preferably, from 50 wt-ppm to 500 wt-ppm. In other preferred embodiments, the additive Irganox®B225 may be present in a composition (e.g., comprising FDME to stabilize this monomer) in an amount from 50 wt-ppm to 1500 wt-ppm or, more preferably, from 50 wt-ppm to 500 wt-ppm.

A number of properties of compositions comprising a monomer, precursor (e.g., prepolymer), or bio-based polymer as described herein may be used as a basis for evaluating the performance of a given additive or combination of additives.

One property, having particular relevance to the commercial value of bio-based polymers, is APHA color, which is determined according to ASTM D1209. APHA color is also referred to as the Hazen scale, as well as the platinum cobalt (Pt/Co) scale. APHA is a color standard named for the American Public Health Association that was originally intended to describe the color of wastewater, but its usage has expanded to include other applications. APHA color (or Hazen or Pt—Co color) is sometimes referred to as a "yellowness index" as it was originally developed to assess the quality of liquids that are clear to yellowish in color.

Another property, having particular relevance to the commercial value of bio-based polymers, is its chromaticity coordinate b* in the L* a* b* color space. This refers to a particular color space of different color systems of the CIE, or Commission Internationale de l+ Echairage (International Commission of Illumination), which color systems were developed as a way to standardize color, or express color values numerically, and thereby remove the subjectivity of the human observer. The CIE 1976 (L* a* b*) color space is based on the opponent-colors theory of color vision, according to which two colors cannot be both green and red at the same time, nor blue and yellow at the same time. Therefore, single values can be used to describe the red/green and the yellow/blue attributes of a sample. In this regard, when a color is expressed using the L a* b* color space, the respective coordinates of L*, a*, and b* denote lightness, the red/green value, and the yellow/blue value.

Accordingly, for purposes of characterizing and monitoring a monomer, precursor (e.g., prepolymer), or bio-based polymer as described herein with respect to its yellow color or the change (development) of yellow color, the value of b* is particularly relevant. The L*, a*, and b* coordinates can be assessed using a colorimeter, for example, a colorimeter as commercially available from Konica Minolta (e.g., model CM-5) and other manufacturers. The values for these coordinates are assigned to a range from −100 to +100.

Compositions comprising a monomer, precursor (e.g., prepolymer), or bio-based polymer as described herein, together with one or more color stabilizing additive compounds, preferably will ideally have an APHA color of less than 10 and a chromaticity coordinate b* in the L* a* b* color space ("chromaticity coordinate b*") of less than 0.5, in terms of lack of color and/or yellowness. In the case of the inventive monomer compositions, these values, particularly with respect to b*, have been selected as especially preferred in consideration of the overall objective of optimally producing a resulting bio-based polymer following further processing that will be characterized by a maximum APHA color of 10 and a maximum b* of 0.65.

Accordingly, it can be appreciated that a preferred context of use of the present invention is in the preparation of a bio-based polymer, such as PEF or PTF, comprising one or more color stabilizing additive compounds as described herein, or otherwise such bio-based polymer in which a composition used in its production ("upstream composition") is stabilized with one or more of such additives. For example, embodiments are directed to a stabilized bio-based polymer, produced from a monomer composition and/or produced from a prepolymer composition, said monomer composition or prepolymer composition having been stabilized with one or more additives, and optionally at the concentration (or wt-ppm) levels, as described herein. Further embodiments are directed to a precursor (e.g., prepolymer) composition, produced from a monomer composition having been stabilized with one or more additives, and optionally at the concentration (or wt-ppm) levels, as described herein. Yet further embodiments are directed to articles (e.g., bottles) comprising a bio-based polymer according to any of the embodiments described above, for example a bio-based polymer comprising one or more additives as described herein and/or a bio-based polymer in which a composition used in its production is (or has been) stabilized with one or more of such additives. According to such embodiments, a stabilized monomer composition, comprising one or more additives, can be considered an upstream composition relative to a precursor (e.g., prepolymer) composition, a bio-based polymer, or an article. A stabilized precursor (e.g., prepolymer) composition, comprising one or more additives, can be considered an upstream composition relative to a bio-based polymer, and a stabilized bio-based polymer composition, comprising one or more additives, can be considered an upstream composition relative to an article.

Compositions comprising a monomer, precursor (e.g., prepolymer), or bio-based polymer as described herein, either (i) further comprising a color stabilizing additive compound and/or otherwise (ii) produced from an upstream composition having been stabilized with such additive, may have an APHA color generally of less than 45, typically less than 20, and often less than 10. Such compositions may, optionally in combination with these APHA color value ranges, have a chromaticity coordinate b* in the L* a* b* color space of generally less than 3, typically less than 1, and often less than 0.5. In the case of solid compositions, the APHA color and/or the chromaticity coordinate b* may be determined by dissolving the composition or sample thereof in a suitable solvent, preferably having little or no contribution to these measured color properties. For example, the solvent may have an APHA color of 0 and/or a chromaticity coordinate b* of 0 (and preferably both), or at least may have an APHA color of less than 3 and/or a chromaticity coordinate b* of less than 0.1 (and preferably both). In the case of a composition comprising FDME, a suitable solvent is a 1:1 (w/w) mixture of isopropanol and acetonitrile, and the color properties of the composition may be determined on the basis of a 6 wt-% solution. In the case of a composition comprising FDCA, a suitable solvent is propylene glycol (PG), and the color properties of the composition (e.g., APHA color and chromaticity coordinate b*) may be determined on the basis of a 1 wt-% solution. An alternative solvent is triethylene glycol, monomethyl ether (TEGMME), and the color properties of a composition comprising FDCA may be determined on the basis of a 3 wt-% solution.

Performance criteria of compositions comprising a monomer, precursor (e.g., prepolymer), or bio-based polymer as described herein, either (i) further comprising a color stabilizing additive compound and/or otherwise (ii) produced from an upstream composition having been stabilized with such additive, may alternatively be measured on the basis of their APHA color and/or chromaticity coordinate b*, following an accelerated aging or accelerated degradation test (or stability test), according to which the composition is subjected to a given temperature for a given time period, in an isolated (sealed) air environment (e.g., in a sealed vial or other container, having air in its headspace).

In representative embodiments, a composition (e.g., comprising FDME) may have an APHA color of less than 20 (e.g., less than 10) and/or a chromaticity coordinate b* of less than 1 (e.g., less than 0.5) (and preferably both), following heating at 120° C. in an isolated air environment for 15 hours. In other representative embodiments, a composition (e.g., comprising FDME) may have an APHA color of less than 20 (e.g., less than 10) and/or a chromaticity coordinate b* of less than 1 (e.g., less than 0.5) (and preferably both), following heating at 150° C. in an isolated air environment for 6 hours. In yet other representative embodiments, a composition (e.g., comprising FDCA) may have an APHA color of less than 40 (e.g., less than 20) and/or a chromaticity coordinate b* of less than 1.5 (e.g., less than 1) (and preferably both), following heating at 100° C. in an isolated air environment for 2 hours.

In the case of a composition comprising FDCA, and particularly in view of its comparably high melting temperature of 342° C. (648° F.), relative to the melting temperature of FDME of 112° C. (234° F.), the accelerated aging or accelerated degradation test, used to determine relevant color properties such as APHA color and/or chromaticity coordinate b*, may be performed in a solution of FDCA and a solvent as described above (e.g., having little or no contribution to the measured color properties). For example, a solution of an FDCA composition, formed by its dissolution in a colorless solvent at a dissolution level of 1-3 wt-%, such as a solution of 1 wt-% FDCA in PG or a solution of 3 wt-% FDCA in TEGMME, may exhibit the color properties as described above. In any such FDCA solution, the color stabilizing additive compound(s) may be present in an amount, or combined amount, as described above (e.g., from 50 wt-ppm to 2000 wt-ppm) with respect to the FDCA in solution.

Preferably, a reference composition, identical in all respects except for the absence of the color stabilizing additive compound, does not meet these properties of APHA color and/or chromaticity coordinate b* (and preferably does not meet both), when subjected to the same accelerated degradation test. That is, the additive in such cases exhibits a significant and demonstrable stabilizing effect. Performance criteria may, for this reason, be deemed to be characteristic of the additive when used in certain compositions (e.g., characteristic of BHA in an FDCA or FDME composition), as opposed to being characteristic of the composition itself.

In other cases, performance criteria may be determined on a basis that is less dependent upon, or even independent of, the initial properties of the composition comprising a monomer, precursor (e.g., prepolymer), or bio-based polymer. For example, in representative embodiments, a composition (e.g., comprising FDME) may exhibit a change in APHA color of less than 20 (e.g., less than 10) and/or may exhibit a change in chromaticity coordinate b* of less than 1 (e.g., less than 0.5) (and preferably both), following heating at 120° C. in an isolated air environment for 15 hours. In other representative embodiments, a composition (e.g., comprising FDME) may exhibit a change in APHA color of less than 20 (e.g., less than 10) and/or may exhibit a change in chromaticity coordinate b* of less than 1 (e.g., less than 0.5) (and preferably both), following heating at 150° C. in an isolated air environment for 6 hours. In yet other representative embodiments, a composition (e.g., comprising FDCA) may exhibit a change in APHA color of less than 40 (e.g., less than 20) and/or may exhibit a change in chromaticity coordinate b* of less than 1.5 (e.g., less than 1) (and preferably both), following heating at 100° C. in an isolated air environment for 2 hours. Preferably, a reference composition, identical in all respects except for the absence of the color stabilizing additive compound, does not meet these properties, in terms of limiting the extent of change of APHA color and/or chromaticity coordinate b* (and preferably does not meet both), when subjected to the same accelerated degradation test.

As described above, color stabilizing additive compound(s) may be added to a monomer described herein, for example to provide a stabilized composition comprising FDCA, FDME, or other monomer. Such additive(s) may alternatively be added to a precursor (e.g., prepolymer). Representative compositions may comprise at least 90 wt-%, at least 95 wt-%, or at least 99 wt-% of such monomer or precursor. To obtain such compositions, it is also possible to incorporate the additive(s) in one or more steps of producing a bio-based polymer (e.g., a copolymer having a furandicarboxylate moiety or residue) as described above.

Representative production methods involve the polymerization of monomers described herein, and particularly 2,5-furandicarboxylic acid (FDCA) and its esterified derivatives, such as its dimethyl ester derivative, namely 2,5-furandicarboxylic acid, dimethyl ester (FDME), with suitable co-monomers such as diols, including ethylene glycol in the case of producing PEF and 1,3-propane diol in the case of producing PTF. Such methods may comprise producing, as a precursor, a prepolymer that is an esterified intermediate such as the reaction product of FDCA with the co-monomer, or a transesterified intermediate such as the reaction product of FDME with the co-monomer. The prepolymer, whether an esterified intermediate or transesterified intermediate, is functionalized with terminal alcohol groups (rather than terminal carboxylate groups of FDCA or terminal methyl groups of FDME) and therefore may then be subjected to polycondensation to provide a bio-based polymer as described herein, and particularly a poly(alkylene furan dicarboxylate) polymer.

According to some embodiments, the monomer used for such production methods (e.g., FDCA or esterified derivative of FDCA), during a storage period prior to producing the esterified intermediate or transesterified intermediate, is stabilized in the presence of a color stabilizing additive compound as described herein. According to other embodiments, the additive is introduced in the step of producing the esterified intermediate or transesterified intermediate, for example the method may include feeding the additive (e.g., batchwise or continuously) to a reaction mixture comprising FDCA or an esterified derivative thereof and the co-monomer. The amount or concentration being fed may be in a range as described above (e.g., from about 50 wt-ppm to about 2000 wt-ppm), with respect to the FDCA or an esterified derivative thereof. According to yet other embodiments, the additive is introduced in the step of polymerizing the esterified intermediate or transesterified intermediate by polycondensation to yield the copolymer (e.g., PEF or PTF). For example, the method may include feeding the additive (e.g., batchwise or continuously) to a reaction mixture comprising the prepolymer, following its formation by esterification or transesterification. The amount or concentration being fed may be in a range as described above (e.g., from about 50 wt-ppm to about 2000 wt-ppm), with respect to the prepolymer.

Processes for producing a bio-based polymer can therefore include both a first, esterification or transesterification step to produce an intermediate (prepolymer), followed by a second, poly condensation step. The first step may be catalyzed by an esterification/transesterification catalyst at a temperature from 150° C. (302° F.) to 250° C. (482° F.), and carried out until the concentration of the starting monomer or its esterified derivative is reduced to less than 3 mol-%. The catalyst may comprise an organotin(IV) compound at 0.01 mol-% to 0.2 mol-%, relative to the starting monomer or its esterified derivative. The intermediate (prepolymer) may optionally be isolated from the reaction mixture of the first reaction step, although generally this is not necessary. The second step of polycondensation may be catalyzed and performed under reduced pressure (e.g., 100 Pascal (Pa) or less), at a temperature in the range of the melting point of the resulting copolymer having a furandicarboxylate moiety, to 30° C. (54° F.) above this temperature, and preferably at a temperature of at least 180° C. (356° F.). The polycondensation catalyst may comprise a tin(II) compound, such as tin(II) oxide or an organotin(II) compound. An additive as described herein may be introduced in either step, to provide a stabilized copolymer.

The prepolymer, as described herein, may therefore be the reaction product of two diol monomers and one monomer bearing a furandicarboxylate moiety that is ultimately present in the backbone of the resulting bio-based polymer. The monomer may be FDCA or an esterified derivative thereof that is formed by the esterification reaction with a suitable alcohol, such as methanol to form FDME or ethanol to form the diethyl ester derivative of FDCA, or otherwise with a phenol. The formation of FDME or other esterified derivative may be carried out, for example, by contacting FDCA with the appropriate alcohol or phenol and a high boiling point solvent (e.g., dimethyl sulfoxide, dimethylacetamide, sulfolane, FDME, γ-butyrolactone, isosorbide or its dimethyl ether, propylene carbonate, adipic acid, isophorone, ethyl phenyl ether, diphenyl ether, dibenzyl ether, aromatic 200 fluid, butyl phenyl ether, methyl heptyl ketone, ethyl phenyl ketone, 2'-hydroxyacetophenone, decahydronaphthalene, tetrahydronaphthalene, etc.) under suitable esterification conditions. These may include a temperature from 30° C. (86° F.) to 350° C. (662° F.) and a pressure from atmospheric pressure to 3.5 megapascal (MPa), and the esterification reaction may be performed together with distillation (according to a reactive distillation process) for separation of the FDME or other esterified derivative. According to some embodiments, the method of forming an esterified derivative of FDCA may include feeding an additive (e.g., batchwise or continuously) as described herein to a reaction mixture comprising FDCA and an alcohol (e.g., methanol or ethanol) or a phenol. The amount or concentration being fed may be in a range as described above (e.g., from 50 wt-ppm to 2000 wt-ppm), with respect to the FDCA.

Further representative production methods include, prior to reacting the monomer (e.g., to produce a prepolymer as described above), producing or synthesizing FDCA or FDME from oxidizing 5-hydroxymethylfurfural (HMF) or a derivative thereof, and, in the case of FDME, subsequently esterifying the FDCA by reaction with methanol (e.g., according to an esterification reaction as described above). The derivative of HMF may be an ester thereof (e.g., 5-methoxymethylfurfural) or may otherwise be a compound selected from the group consisting of 5-methylfurfural, 5-(chloromethyl)furfural, 5-methylfuroic acid, 5-chloromethylfuroic acid, and 2,5-dimethylfuran. Oxidation of HMF or a derivative thereof may be performed under oxidation conditions and in the presence of an oxidizing agent (e.g., air or other oxygen-containing gas) and an oxidizing catalyst, for example a catalyst comprising both Co and Mn and a source of bromine. Representative oxidation conditions include a temperature from 125° C. (257° F.) to 300° C. (572° F.). According to some embodiments, the method of forming FDCA may include feeding an additive (e.g., batchwise or continuously) as described herein to a reaction mixture comprising 5-hydroxymethylfurfural (HMF) or a derivative thereof and an oxidant. The amount or concentration being fed may be in a range as described above (e.g., from 50 wt-ppm to 2000 wt-ppm), with respect to the HMF or a derivative thereof.

Accordingly, it can be appreciated that a number of opportunities exist for employing color stabilizing additive compounds as described herein, prior to obtaining the bio-based polymer. Such additives may be fed, for example, during or following reaction steps involving (i) the oxidation of HMF or derivative thereof, (ii) the esterification of FDCA, (iii) the production of a prepolymer, and/or (iv) the polycondensation of a prepolymer. The additive(s) may remain in the bio-based polymer or may optionally be removed, for example, during or following any of the reaction steps involving (ii), (iii), or (iv) above. Removal may be performed using a suitable extraction agent, in which the additive(s) is/are selectively soluble.

The following examples are set forth as representative of the present invention. These examples are illustrative and not to be construed as limiting the scope of the invention as defined in the appended claims. The parts per million (ppm) values in the examples below are by weight (i.e., wt-ppm)

COMPARATIVE EXAMPLES

Color Degradation of FDME

Color development in FDME was determined over periods of accelerated degradation testing. In each test, a 10-gram sample of FDME was charged to a vial having 20 ml of air headspace. The vial was then placed in a heating block, set to the temperature at which color stability was to be measured. Once solid was melted and the desired temperature reached, a timer was activated and, following a predetermined time period of the test, the vial was removed and allowed to cool to ambient conditions. Approximately 240 mg of the solid was then dissolved in 3.76 grams of a 1:1 (w/w) mixture of isopropanol (IPA) and acetonitrile, which mixture was referred to as the "matrix" below. The solid and matrix were sonicated until complete dissolution, and the color of the solution was established using a Konica Minolta CM-5 colorimeter.

Tables 1-3 below show the results of tests performed on reference compositions, without a color stabilizing additive compound. The APHA color values and chromaticity coordinates $L^*$ $a^*$ $b^*$ were determined for (i) the matrix initially, (ii) the FDME initially, and (iii) FDME samples, following heating at 120° C. (248° F.) for 15 hours (Table 1), or at 150° C. (302° F.) for 15 hours (Table 2), or at 120° C. (248° F.) for 48 hours (Table 3).

TABLE 1

Matrix and FDME Color Data, 120° C., 15 h

| | Data Name | [Antioxidant] ppm | L*(C) | a*(C) | b*(C) | APHA |
|---|---|---|---|---|---|---|
| Target | 1:1 IPA/Acetonitrile Matrix | 0 | 99.98 | 0 | 0 | 0 |
| — | FDME | 0 | 99.79 | −0.01 | 0.07 | 1 |
| 1 | FDME #1, 120° C., 15 h | 0 | 99.66 | 0.05 | 0.54 | 19 |
| 2 | FDME #2, 120° C., 15 h | 0 | 99.43 | −0.03 | 0.56 | 20 |
| 3 | FDME #3, 120° C., 15 h | 0 | 99.73 | −0.02 | 0.63 | 23 |
| 4 | FDME #4, 120° C., 15 h | 0 | 99.39 | −0.03 | 0.58 | 21 |
| 5 | FDME #5, 120° C., 15 h | 0 | 99.67 | −0.02 | 0.67 | 25 |
| — | Average | | 99.58 | −0.01 | 0.60 | 22 |
| — | Standard Deviation | | 0.13 | 0.03 | 0.04 | 2 |

TABLE 2

Matrix and FDME Color Data, 150° C., 15 h

| | Data Name | Sample # | L*(C) | a*(C) | b*(C) | APHA |
|---|---|---|---|---|---|---|
| Target | 1:1 IPA/Acetonitrile Matrix | 0 | 100.01 | −0.01 | 0.02 | 0 |
| — | FDME | 0 | 99.79 | −0.01 | 0.07 | 1 |
| 1 | FDME #1, 150° C., 15 h | 1 | 99.74 | 0.07 | 0.56 | 21 |
| 2 | FDME #2, 150° C., 15 h | 2 | 99.89 | −0.09 | 0.65 | 24 |
| 3 | FDME #3, 150° C., 15 h | 3 | 99.91 | 0.03 | 0.56 | 20 |
| 4 | FDME #4, 150° C., 15 h | 4 | 99.74 | 0.01 | 0.58 | 21 |
| 5 | FDME #5, 150° C., 15 h | 5 | 99.76 | 0.04 | 0.68 | 25 |
| | Average | | 99.81 | 0.01 | 0.61 | 22 |
| | Standard Deviation | | 0.08 | 0.05 | 0.05 | 2 |

TABLE 3

Matrix and FDME Color Data, 120° C., 48 h

| | Data Name | Sample # | L*(C) | a*(C) | b*(C) | APHA |
|---|---|---|---|---|---|---|
| Target | 1:1 IPA/Acetonitrile Matrix | 0 | 99.98 | 0 | 0 | 0 |
| — | FDME | 0 | 99.79 | −0.01 | 0.07 | 1 |
| 1 | FDME #1, 120° C., 48 h | 1 | 99.99 | 0.00 | 0.72 | 24 |
| 2 | FDME #2, 120° C., 48 h | 2 | 99.86 | −0.02 | 0.78 | 25 |
| 3 | FDME #3, 120° C., 48 h | 3 | 99.79 | −0.01 | 0.92 | 32 |
| 4 | FDME #4, 120° C., 48 h | 4 | 99.42 | −0.04 | 0.82 | 26 |
| 5 | FDME #5, 120° C., 48 h | 5 | 99.84 | −0.01 | 0.76 | 25 |
| | Average | | 99.78 | −0.02 | 0.8 | 26 |
| | Standard Deviation | | 0.19 | 0.01 | 0.07 | 3 |

The initial FDME samples were obtained from a highly pure source, as is evident from the values in the third row of the Tables 1-3 above. However, following exposure to all temperatures tested for the respective time periods tested, the APHA color exceeded 10 and the chromaticity coordinate $b^*$ exceeded 0.5.

EXAMPLES

Color Stabilization of FDME

Color stabilizing additive compounds were tested for their ability to prevent color development in FDME samples, during periods of accelerated degradation testing. The tests were performed as described above, except, prior to heating, each 10-gram sample of FDME was charged with a measured amount of additive to the vial. In the tables below, the APHA color values and chromaticity coordinates L* a* b* are shown as determined for (i) the matrix initially, (ii) the FDME initially, and (iii) FDME samples, following heating with varying wt-ppm levels of color stabilizing additive compounds. In particular, the results obtained for tests at 120° C. (248° F.) for 15 hours with BHA are shown in Table 4.

TABLE 4

FDME with BHA Additive, 120° C., 15 h

|  | Data Name | [BHA] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 100 | 0 | 0 | — | 0 | — |
| — | FDME | 0 | 99.79 | −0.01 | 0.07 | — | 1 | — |
| 1 | FDME, 120° C., 15 h | 0 | 99.58 | −0.01 | 0.60 | — | 22 | — |
| 2 | FDME, 50 ppm BHA, 120° C., 15 h | 50 | 99.72 | 0.00 | 0.31 | 0.29 | 13 | 9 |
| 3 | FDME, 100 ppm BHA, 120° C., 15 h | 100 | 99.53 | −0.03 | 0.39 | 0.21 | 15 | 7 |
| 4 | FDME, 200 ppm BHA, 120° C., 15 h | 200 | 99.48 | −0.03 | 0.41 | 0.19 | 16 | 6 |
| 5 | FDME, 300 ppm BHA, 120° C., 15 h | 300 | 99.58 | −0.05 | 0.46 | 0.14 | 17 | 5 |
| 6 | FDME, 500 ppm BHA, 120° C., 15 h | 500 | 99.77 | −0.06 | 0.51 | 0.09 | 18 | 4 |
| 7 | FDME, 1500 ppm BHA, 120° C., 15 h | 1500 | 99.77 | −0.06 | 0.72 | −0.12 | 23 | −1 |

According to these results, BHA had a color stabilizing effect on FDME, particularly in view of the decreased values of APHA color and the chromaticity coordinate b*, relative to the reference composition in the fourth row of the table above.

The results obtained for tests at 130° C. (266° F.) for 6 hours with BHA are shown in Table 5.

TABLE 5

FDME with BHA Additive, 130° C., 6 h

|  | Data Name | [BHA] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 99.99 | −0.01 | 0 | — | 0 | — |
| — | FDME | 0 | 99.79 | −0.01 | 0.07 | — | 1 | — |
| 1 | FDME, 130° C., 6 h | 0 | 99.75 | −0.03 | 0.13 | — | 3 | — |
| 2 | FDME 50 ppm BHA, 130° C., 6 h | 50 | 99.81 | −0.01 | 0.04 | 0.09 | 0 | 3 |
| 3 | FDME 100 ppm BHA, 130° C., 6 h | 100 | 99.76 | −0.01 | 0.06 | 0.07 | 1 | 2 |
| 4 | FDME, 200 ppm BHA, 130° C., 6 h | 200 | 99.78 | −0.02 | 0.09 | 0.04 | 1 | 2 |
| 5 | FDME, 500 ppm BHA, 130° C., 6 h | 500 | 99.79 | −0.02 | 0.11 | 0.02 | 2 | 1 |
| 6 | FDME, 1000 ppm BHA, 130° C., 6 h | 1000 | 99.72 | −0.01 | 0.22 | −0.09 | 10 | −7 |
| 7 | FDME, 500 ppm TBHQ, 130° C., 6 h | 500 | 99.78 | −0.15 | 0.42 | −0.29 | 15 | −12 |

These results further illustrate that BHA had a color stabilizing effect on FDME, particularly in view of the decreased values of APHA color and the chromaticity coordinate b*, relative to the reference composition in the fourth row of the table above.

The results obtained for tests at 150° C. (302° F.) for 6 hours with BHA are shown in Table 6.

TABLE 6

FDME with BHA Additive, 150° C., 6 h

|  | Data Name | [Antioxidant] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 99.99 | 0.01 | −0.01 | — | 0 | — |
| — | FDME | 0 | 99.79 | −0.01 | 0.07 | — | 1 | — |
| 1 | FDME, 150° C., 6 h | 0 | 99.71 | −0.08 | 0.58 | — | 15 | — |
| 2 | FDME, 50 ppm BHA, 150° C., 6 h | 50 | 99.77 | −0.01 | 0.05 | 0.53 | 1 | 14 |
| 3 | FDME, 100 ppm BHA, 150° C., 6 h | 100 | 99.80 | −0.02 | 0.07 | 0.51 | 1 | 14 |
| 4 | FDME, 200 ppm BHA, 150° C., 6 h | 200 | 99.82 | −0.04 | 0.14 | 0.44 | 3 | 12 |
| 5 | FDME, 300 ppm BHA, 150° C., 6 h | 300 | 99.79 | −0.06 | 0.16 | 0.42 | 4 | 11 |
| 6 | FDME, 400 ppm BHA, 150° C., 6 h | 400 | 99.75 | −0.07 | 0.24 | 0.34 | 9 | 6 |
| 7 | FDME, 600 ppm BHA, 150° C., 6 h | 600 | 99.60 | −0.10 | 0.30 | 0.28 | 11 | 4 |
| 8 | FDME, 1500 ppm BHA, 150° C., 6 h | 1500 | 99.58 | −0.13 | 1.10 | −0.52 | 39 | −24 |

These results further illustrate that BHA had a color stabilizing effect on FDME, particularly in view of the decreased values of APHA color the chromaticity coordinate b*, relative to the reference composition in the fourth row of the table above. At BHA additive amounts of 50-600 ppm, b* was reduced to less than 0.5. In addition, at BHA additive amounts of 50-400 ppm, APHA color was also reduced to less than 10.

The results obtained for tests at 150° C. (302° F.) for 6 hours with TBHQ are shown in Table 7.

TABLE 7

FDME with TBHQ Additive, 150° C., 6 h

| | Data Name | [Antioxidant] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 99.99 | 0.01 | −0.01 | — | 0 | — |
| — | FDME | 0 | 99.79 | −0.01 | 0.07 | — | 1 | — |
| 1 | FDME, 150° C., 6 h | 0 | 99.67 | −0.09 | 0.55 | — | 18 | — |
| 2 | FDME, 100 ppm TBHQ, 150° C., 6 h | 0 | 99.75 | −0.13 | 0.69 | −0.14 | 24 | −6 |
| 3 | FDME, 100 ppm TBHQ, 150° C., 6 h | 100 | 99.72 | −0.15 | 0.78 | −0.23 | 26 | −8 |
| 4 | FDME, 200 ppm TBHQ, 150° C., 6 h | 200 | 99.96 | −0.20 | 1.17 | −0.62 | 38 | −20 |
| 5 | FDME, 300 ppm TBHQ, 150° C., 6 h | 300 | 99.67 | −0.38 | 1.57 | −1.02 | 46 | −28 |
| 6 | FDME, 500 ppm TBHQ, 150° C., 6 h | 500 | 99.58 | −0.43 | 2.42 | −1.87 | 60 | −42 |
| 7 | FDME, 1500 ppm TBHQ, 150° C., 6 h | 1500 | 99.92 | −0.44 | 3.46 | −2.91 | 81 | −63 |

The results obtained for tests at 150° C. (302° F.) for 6 hours with DMP are shown in Table 8.

TABLE 8

FDME with DMP Additive, 150 Deg. C, 6 h

| | Data Name | [Antioxidant] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 100.01 | 0.00 | 0.01 | — | 0 | — |
| — | FDME | 0 | 99.79 | −0.01 | 0.07 | — | 1 | — |
| 1 | FDME, 150° C., 6 h | 0 | 99.71 | −0.08 | 0.58 | — | 15 | — |
| 2 | FDME, 50 ppm DMP, 150° C., 6 h | 50 | 99.80 | 0.15 | 0.66 | −0.08 | 24 | −9 |
| 3 | FDME, 100 ppm DMP, 150° C., 6 h | 100 | 98.65 | 0.19 | 0.61 | −0.03 | 23 | −8 |
| 4 | FDME, 200 ppm DMP, 150° C., 6 h | 200 | 98.85 | 0.23 | 0.50 | 0.08 | 20 | −5 |
| 5 | FDME, 300 ppm DMP, 150° C., 6 h | 300 | 99.49 | 0.05 | 0.30 | 0.28 | 14 | 1 |
| 6 | FDME, 500 ppm DMP, 150° C., 6 h | 500 | 99.84 | 0.02 | 0.16 | 0.42 | 6 | 9 |
| 7 | FDME, 1500 ppm DMP, 150° C., 6 h | 1500 | 99.78 | −0.01 | 0.27 | 0.31 | 12 | 3 |

These results illustrate that DMP had a color stabilizing effect on FDME. At DMP additive amounts of 200-1500 ppm, the chromaticity coordinate b* was reduced to less than 0.5. At DMP additive amounts of about 500 ppm (e.g., from about 400 ppm to about 600 ppm), APHA color was also reduced to less than 10.

The results obtained for tests at 150° C. (302° F.) for 6 hours with DTMP are shown in Table 9.

TABLE 9

FDME with DTMP Additive, 150° C., 6 h

| | Data Name | [Antioxidant] ppm | L*(C) | a* (C) | b*(C) | Δ b* | APHA | Δ APHA |
|---|---|---|---|---|---|---|---|---|
| Target | 1:1 IPA/Acetonitrile Matrix | 0 | 99.99 | 0.00 | 0.00 | — | 0 | — |
| — | FDME | 0 | 99.79 | −0.01 | 0.07 | — | 1 | — |
| 1 | FDME, 150° C., 6 h | 0 | 99.71 | −0.08 | 0.58 | — | 15 | — |
| 2 | FDME, 50 ppm DTMP, 150° C., 6 h | 50 | 99.76 | 0.05 | 0.40 | 0.18 | 11 | 4 |
| 3 | FDME, 100 ppm DTMP, 150° C., 6 h | 100 | 99.59 | 0.14 | 0.38 | 0.20 | 11 | 4 |
| 4 | FDME, 200 ppm DTMP, 150° C., 6 h | 200 | 99.51 | 0.22 | 0.51 | 0.07 | 15 | 0 |
| 5 | FDME, 300 ppm DTMP, 150° C., 6 h | 300 | 98.95 | 0.18 | 0.63 | −0.05 | 23 | −8 |
| 6 | FDME, 500 ppm DTMP, 150° C., 6 h | 500 | 98.78 | 0.30 | 1.10 | −0.52 | 43 | −28 |
| 7 | FDME, 1500 ppm DTMP, 150° C., 6 h | 1500 | 98.34 | 0.45 | 1.89 | −1.31 | 66 | −51 |

These results illustrate that DTMP had a color stabilizing effect on FDME. At DTMP additive amounts of 50-100 ppm, the chromaticity coordinate b* was reduced to less than 0.5.

The results obtained for tests at 150° C. (302° F.) for 6 hours with XDPA are shown in Table 10.

TABLE 10

FDME with XDPA Additive, 150° C., 6 h

|   | Data Name | [Antioxidant] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 100.01 | 0.00 | 0.01 | — | 0 | — |
| — | FDME | 0 | 99.79 | −0.01 | 0.07 | — | 1 | — |
| 1 | FDME, 150° C., 6 h | 0 | 99.71 | −0.08 | 0.58 | — | 15 | — |
| 2 | FDME, 50 ppm XDPA, 150° C., 6 h | 50 | 99.57 | 0.07 | 0.55 | 0.03 | 14 | 1 |
| 3 | FDME, 100 ppm XDPA, 150° C., 6 h | 100 | 99.93 | 0.19 | 0.41 | 0.17 | 12 | 3 |
| 4 | FDME, 200 ppm XDPA, 150° C., 6 h | 200 | 99.52 | 0.04 | 0.33 | 0.25 | 11 | 4 |
| 5 | FDME, 300 ppm XDPA, 150° C., 6 h | 300 | 99.64 | −0.04 | 0.41 | 0.17 | 12 | 3 |
| 6 | FDME, 500 ppm XDPA, 150° C., 6 h | 500 | 99.57 | −0.08 | 0.42 | 0.16 | 13 | 2 |
| 7 | FDME, 1500 ppm XDPA, 150° C., 6 h | 1500 | 99.73 | −0.05 | 0.34 | 0.24 | 12 | 3 |

These results illustrate that XDPA had a color stabilizing effect on FDME, particularly in view of the decreased values of APHA color and the chromaticity coordinate b*, relative to the reference composition in the fourth row of the table above. At XDPA additive amounts of 100-1500 ppm, b* was reduced to less than 0.5.

The results obtained for tests at 150° C. (302° F.) for 6 hours with PETC are shown in Table 11.

TABLE 11

FDME with PETC Additive, 150° C., 6 h

|   | Data Name | [Antioxidant] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 100.01 | 0.00 | 0.01 | — | 0 | — |
| — | FDME | 0 | 99.79 | −0.01 | 0.07 | — | 1 | — |
| 1 | FDME, 150° C., 6 h | 0 | 99.71 | −0.08 | 0.58 | — | 15 | — |
| 2 | FDME, 50 ppm PETC, 150° C., 6 h | 50 | 98.55 | 0.18 | 0.87 | −0.29 | 33 | −18 |
| 3 | FDME, 100 ppm PETC, 150° C., 6 h | 100 | 98.33 | 0.20 | 0.81 | −0.23 | 31 | −16 |
| 4 | FDME, 200 ppm PETC, 150° C., 6 h | 200 | 99.77 | 0.11 | 0.26 | 0.32 | 13 | 2 |
| 5 | FDME, 300 ppm PETC, 150° C., 6 h | 300 | 99.50 | 0.15 | 0.36 | 0.22 | 16 | −1 |
| 6 | FDME, 500 ppm PETC, 150° C., 6 h | 500 | 99.78 | 0.12 | 0.21 | 0.37 | 11 | 4 |
| 7 | FDME, 1500 ppm PETC, 150° C., 6 h | 1500 | 99.68 | 0.11 | 0.30 | 0.28 | 14 | 1 |

These results illustrate that PETC had a color stabilizing effect on FDME. At PETC additive amounts of 200-1500 ppm, the chromaticity coordinate b* was reduced to less than 0.5.

The results of tests at 150° C. (302° F.) for 6 hours with Irganox®245 are in Table 12.

TABLE 12

FDME with Irganox ®245 Additive, 150° C., 6 h

|   | Data Name | [Antioxidant] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 100.01 | 0.00 | 0.01 | — | 0 | — |
| — | FDME | 0 | 99.79 | −0.01 | 0.07 | — | 1 | — |
| 1 | FDME, 150° C., 6 h | 0 | 99.71 | −0.08 | 0.58 | — | 15 | — |
| 2 | FDME, 50 ppm Irganox 245, 150° C., 6 h | 50 | 99.62 | 0.08 | 0.22 | 0.36 | 10 | 5 |
| 3 | FDME, 100 ppm Irganox 245, 150° C., 6 h | 100 | 99.48 | 0.08 | 0.33 | 0.25 | 13 | 2 |
| 4 | FDME, 200 ppm Irganox 245, 150° C., 6 h | 200 | 99.65 | 0.04 | 0.40 | 0.18 | 16 | −1 |
| 5 | FDME, 500 ppm Irganox 245, 150° C., 6 h | 500 | 99.43 | 0.06 | 0.41 | 0.17 | 17 | −2 |
| 6 | FDME, 1500 ppm Irganox 245, 150° C., 6 h | 1500 | 99.60 | 0.01 | 0.50 | 0.08 | 19 | −4 |

These results illustrate that Irganox®245 had a color stabilizing effect on FDME. At Irganox®245 additive amounts of 50-1500 ppm, the chromaticity coordinate b* was reduced to less than 0.5. At Irganox®245 additive amounts of about 50 ppm (e.g., from about 50 ppm to about 100 ppm), APHA color was also reduced to 10.

The results obtained for tests at 150° C. (302° F.) for 6 hours with Irganox®B900 are shown in Table 13.

TABLE 13

FDME with Irganox ®B900 Additive, 150° C., 6 h

| | Data Name | [Antioxidant] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 100.01 | 0.00 | 0.01 | — | 0 | — |
| — | FDME | 0 | 99.79 | −0.01 | 0.07 | — | 1 | — |
| 1 | FDME, 150° C., 6 h | 0 | 99.71 | −0.08 | 0.58 | — | 15 | — |
| 2 | FDME, 50 ppm Irganox B900, 150° C., 6 h | 50 | 99.66 | −0.02 | 0.27 | 0.31 | 10 | 5 |
| 3 | FDME, 100 ppm Irganox B900, 150° C., 6 h | 100 | 99.61 | −0.05 | 0.25 | 0.33 | 10 | 5 |
| 4 | FDME, 200 ppm Irganox B900, 150° C., 6 h | 200 | 99.29 | −0.03 | 0.17 | 0.41 | 7 | 8 |
| 5 | FDME, 500 ppm Irganox B900, 150° C., 6 h | 500 | 99.74 | −0.04 | 0.22 | 0.36 | 8 | 7 |
| 6 | FDME, 1500 ppm Irganox B900, 150° C., 6 h | 1500 | 99.65 | −0.06 | 0.33 | 0.25 | 13 | 2 |

These results illustrate that Irganox®B900 had a color stabilizing effect on FDME, particularly in view of the decreased values of APHA color and the chromaticity coordinate b*, relative to the reference composition in the fourth row of the table above. At Irganox®B900 additive amounts of 50-1500 ppm, b* was reduced to less than 0.5. In addition, at Irganox®B900 additive amounts of 50-500 ppm, APHA color was also reduced to 10 or less.

The results obtained for tests at 150° C. (302° F.) for 6 hours with Irganox®B225 are shown in Table 14.

TABLE 14

FDME with Irganox ®B225 Additive, 150° C., 6 h

| | Data Name | [Antioxidant] ppm | L*(C) | a*(C) | b*(C) | Δ b* | APHA | Δ APHA |
|---|---|---|---|---|---|---|---|---|
| Target | 1:1 IPA/Acetonitrile Matrix | 0 | 99.99 | 0.00 | 0.00 | — | 0 | — |
| — | FDME | 0 | 99.79 | −0.01 | 0.07 | — | 1 | — |
| 1 | FDME, 150° C., 6 h | 0 | 99.71 | −0.08 | 0.58 | — | 15 | — |
| 2 | FDME, 50 ppm Irganox B225, 150° C., 6 h | 50 | 99.76 | −0.01 | 0.17 | 0.41 | 7 | 8 |
| 3 | FDME, 100 ppm Irganox B225, 150° C., 6 h | 100 | 99.58 | −0.04 | 0.18 | 0.40 | 7 | 8 |
| 4 | FDME, 200 ppm Irganox B225, 150° C., 6 h | 200 | 99.81 | −0.02 | 0.24 | 0.34 | 9 | 6 |
| 5 | FDME, 500 ppm Irganox B225, 150° C., 6 h | 500 | 99.85 | −0.06 | 0.26 | 0.32 | 9 | 6 |
| 6 | FDME, 1500 ppm Irganox B225, 150° C., 6 h | 1500 | 99.63 | −0.01 | 0.30 | 0.28 | 12 | 3 |

These results illustrate that Irganox®B225 had a color stabilizing effect on FDME, particularly in view of the decreased values of APHA color and the chromaticity coordinate b*, relative to the reference composition in the fourth row of the table above. At Irganox®B225 additive amounts of 50-1500 ppm, b* was reduced to less than 0.5. In addition, at Irganox®B225 additive amounts of 50-500 ppm, APHA color was also reduced to less than 10.

Color Stabilization of FDCA

Color stabilizing additive compounds were tested for their ability to prevent color development in FDCA samples, during periods of accelerated degradation testing. In a first set of tests, a 300 mg sample of FDCA was dissolved in 9700 mg of triethylene glycol monomethyl ether (TEGMME) to provide a 3 wt-% solution. A reference composition of FDCA without any additive was heated to 100° C. (212° F.) for 2 hours in an air environment, after which time the composition was allowed to cool to ambient conditions. Various compositions having color stabilizing additive compounds alone, namely BHA, Irganox®245, Irganox®B900, Irganox®B225, Dovernox®10, and Dovernox®76 were subjected to these heating conditions. Also, each of these additives was combined with a composition comprising the 3 wt-% solution of FDCA as described above, at an addition level of 100 ppm, and the resulting stabilized compositions were also subjected to these heating conditions.

The color of the reference composition, additives alone, and stabilized FDCA compositions comprising 100 ppm of these additives, was established using a Konica Minolta CM-5 colorimeter. Table 15 below shows the APHA color values and chromaticity coordinates L* a* b* that were determined for the samples.

TABLE 15

FDCA, 3 wt-% in TEGMME, Stabilization with Various Additives, 100° C., 2 h

| AO | FDCA (wt. %) | AO (ppm) | Temp (° C.) | Time (min) | Gas | L* | a* | b* | APHA |
|---|---|---|---|---|---|---|---|---|---|
| — | — | — | — | — | Air | 99.99 | 0.03 | 0 | 0 |
| — | — | — | 100 | 120 | Air | 99.86 | 0.03 | 0.09 | 2 |
| — | 3 | — | 100 | 120 | Air | 99.54 | −0.90 | 2.11 | 102 |
| BHA | — | 100 | 100 | 120 | Air | 100 | 0.02 | 0.01 | 0 |
| BHA | 3 | 100 | 100 | 120 | Air | 99.81 | −0.41 | 0.86 | 25 |
| Irganox 245 | — | 100 | 100 | 120 | Air | 99.88 | 0.03 | 0.01 | 1 |
| Irganox 245 | 3 | 100 | 100 | 120 | Air | 99.67 | −0.44 | 1.01 | 31 |
| Irganox B900 | — | 100 | 100 | 120 | Air | 99.94 | 0.06 | 0.05 | 2 |
| Irganox B900 | 3 | 100 | 100 | 120 | Air | 99.76 | −0.33 | 0.94 | 27 |
| Irganox B225 | — | 100 | 100 | 120 | Air | 99.92 | 0.01 | 0.03 | 1 |
| Irganox B225 | 3 | 100 | 100 | 120 | Air | 99.89 | −0.48 | 0.79 | 24 |
| Dovernox 10 | — | 100 | 100 | 120 | Air | 99.84 | 0.02 | 0.01 | 1 |
| Dovernox 10 | 3 | 100 | 100 | 120 | Air | 99.79 | −0.61 | 1.20 | 46 |
| Dovernox 76 | — | 100 | 100 | 120 | Air | 99.80 | −0.01 | 0.04 | 2 |
| Dovernox 76 | 3 | 100 | 100 | 120 | Air | 99.91 | −0.53 | 0.68 | 21 |

These results illustrate that all tested additives had a color stabilizing effect on FDCA, particularly in view of the decreased values of APHA color and the chromaticity coordinate b*, relative to the reference composition in the fourth row of the table above.

Additional tests were performed according to the procedures described above, but by dissolving a 100 mg sample of FDCA in 9900 mg of propylene glycol (PG) to provide a 1 wt-% solution. Varying amounts of additives were tested for their color stabilization of FDCA, and the APHA color values and chromaticity coordinates L* a* b* were determined as shown in Table 16 below.

TABLE 16

FDCA, 1 wt-% in PG, Stabilization with Various Additives, 100° C., 2 h

| FDCA (wt. %) | AO | AO (ppm) | Temp (° C.) | Time (min) | Gas | L* | a* | b* | APHA |
|---|---|---|---|---|---|---|---|---|---|
| — | — | — | — | — | Air | 99.99 | 0.01 | 0 | 0 |
| — | — | — | 100 | 120 | Air | 99.94 | −0.01 | 0.03 | 0 |
| 1 | — | — | 100 | 120 | Air | 99.75 | −0.91 | 1.87 | 81 |
| — | BHA | 100 | 100 | 120 | Air | 100 | −0.02 | 0 | 0 |
| 1 | BHA | 100 | 100 | 120 | Air | 99.87 | −0.26 | 0.49 | 26 |
| 1 | BHA | 500 | 100 | 120 | Air | 99.69 | −0.17 | 0.33 | 17 |
| — | Irganox 245 | 100 | 100 | 120 | Air | 99.88 | 0.02 | 0 | 0 |
| 1 | Irganox 245 | 100 | 100 | 120 | Air | 99.74 | −0.33 | 0.88 | 24 |
| 1 | Irganox 245 | 300 | 100 | 120 | Air | 99.71 | −0.34 | 0.96 | 27 |
| 1 | Irganox 245 | 600 | 100 | 120 | Air | 99.69 | −0.19 | 0.63 | 21 |
| 1 | Irganox 245 | 1000 | 100 | 120 | Air | 99.83 | −0.08 | 0.28 | 11 |
| — | Irganox B900 | 100 | 100 | 120 | Air | 99.91 | 0.04 | 0.01 | 1 |
| 1 | Irganox B900 | 100 | 100 | 120 | Air | 99.83 | −0.05 | 0.52 | 18 |
| 1 | Irganox B900 | 300 | 100 | 120 | Air | 99.81 | −0.11 | 0.64 | 20 |
| 1 | Irganox B900 | 600 | 100 | 120 | Air | 99.42 | −0.18 | 3.55 | 145 |
| 1 | Irganox B900 | 1000 | 100 | 120 | Air | 99.51 | −0.24 | 4.21 | 187 |
| — | Irganox B225 | 100 | 100 | 120 | Air | 99.96 | 0.01 | 0 | 0 |
| 1 | Irganox B225 | 100 | 100 | 120 | Air | 99.89 | 0.03 | 0.54 | 25 |
| — | Dovernox 10 | 100 | 100 | 120 | Air | 99.91 | 0.01 | 0.02 | 1 |
| 1 | Dovernox 10 | 100 | 100 | 120 | Air | 99.82 | −0.14 | 0.65 | 20 |
| — | Dovernox 76 | 100 | 100 | 120 | Air | 99.92 | 0.01 | 0.03 | 2 |
| 1 | Dovernox 76 | 100 | 100 | 120 | Air | 99.86 | −0.11 | 0.71 | 27 |
| 1 | Dovernox 76 | 300 | 100 | 120 | Air | 99.81 | −0.18 | 0.56 | 25 |

These results illustrate a color stabilizing effect on FDCA, for a number of the tested additives. The chromaticity coordinate b* was reduced to less than 0.5 at BHA additive amounts of 100-500 ppm and at Irganox®245 additive amounts of about 1000 ppm (e.g., from about 800 ppm to about 1200 ppm).

Overall, aspects of the invention relate to the use of color stabilizing additive compounds to improve color stability of monomers and other reactants in the formation of bio-based polymers, such as those having furandicarboxylate moieties in the polymer backbone. Specific embodiments and examples described herein are for illustrative purposes only, and not limiting of the invention as set forth in the appended claims. Those having skill in the art, with the knowledge gained from the present disclosure, will recognize that various changes can be made to stabilized compositions and methods for producing stabilized bio-based polymers, in attaining these and other advantages, without departing from the scope of the present disclosure.

The invention claimed is:

1. A monomer composition, consisting essentially of:
   2,5-furan dicarboxylic acid (FDCA) or an esterified derivative thereof and a color stabilizing additive compound, wherein the esterified derivative is formed by the esterification of FDCA with methanol, ethanol, or phenol.

2. The monomer composition of claim 1, wherein the color stabilizing additive compound is a substituted phenol;
   wherein the substituted phenol is a methoxy-substituted phenol or a tert-butyl-substituted phenol.

3. The monomer composition of claim 1, wherein the color stabilizing additive compound is selected from the group consisting of butylated hydroxyanisole (BHA); 2,6-dimethoxyphenol (DMP); 2,6-di-tert-butyl-4-methoxylphenol (DTMP); pentaerythritol tetrakis[3-[3,5-di-tert-butyl-4-hydroxyphenyl]propionate (PETC); 2-tert-butylhydroquinone (TBHQ); 4,4'-bis($\alpha,\alpha$-dimethylbenzyl) diphenylamine (XDPA); ethylenebis (oxyethylene) bis-(3-(5-tert-butyl-4-hydroxy-m-tolyl)-propionate); tris(2,4-di-tert-butylphenyl)phosphite; octadecyl-3-(3,5-di-tert-butyl-4-hydroxyphenyl)-propionate, ascorbic acid, and mixtures thereof.

4. The monomer composition of claim 1, wherein the monomer composition consists essentially of, as the esterified derivative of FDCA, a dialkyl ester derivative formed by esterification of FDCA with methanol, ethanol, or phenol.

5. The monomer composition of claim 4, wherein the monomer composition consists essentially of, as the dialkyl ester derivative of FDCA, a dimethyl ester derivative that is 2,5-furan dicarboxylic acid dimethyl ester (FDME).

6. The monomer composition of claim 5, wherein the color stabilizing additive compound is present in the monomer composition in an amount from about 50 to about 2000 parts per million by weight (wt-ppm).

7. The monomer composition of claim 5, wherein the monomer composition exhibits an American Public Health Association (APHA) color of less than 10 and a chromaticity coordinate $b^*$ in the $L^* a^* b^*$ color space of less than 0.5 after accelerated degradation testing at 120° C. in an isolated air environment for 15 hours.

8. The monomer composition of claim 5, wherein the monomer composition exhibits an American Public Health Association (APHA) color of less than 10 and a chromaticity coordinate $b^*$ in the $L^* a^* b^*$ color space of less than 0.5 after accelerated degradation testing at 150° C. in an isolated air environment for 6 hours.

9. The monomer composition of claim 1, wherein the monomer composition consists essentially of FDCA.

10. The monomer composition of claim 9, wherein a solution of the monomer composition, formed by dissolution in a colorless solvent at a dissolution level of 1-3% by weight of FDCA, exhibits a chromaticity coordinate $b^*$ in the $L^* a^* b^*$ color space of less than 0.5 after accelerated degradation testing at 100° C. in an isolated air environment for 2 hours.

11. The monomer composition of claim 10,
    wherein the solution of the monomer composition, formed by dissolution in the colorless solvent which is a propylene glycol, at a dissolution level of 1% by weight of FDCA, exhibits a chromaticity coordinate $b^*$ in the $L^* a^* b^*$ color space of less than 0.5 after accelerated degradation testing at 100° C. in an isolated air environment for 2 hours.

12. The monomer composition of claim 10,
    wherein the solution of the monomer composition, formed by dissolution in the colorless solvent which is triethylene glycol monomethyl ether, at a dissolution level of 3% by weight of FDCA, exhibits a chromaticity coordinate $b^*$ in the $L^* a^* b^*$ color space of less than 0.5 after accelerated degradation testing at 100° C. in an isolated air environment for 2 hours.

13. The monomer composition of claim 10, wherein, in the solution of the monomer composition, the color stabilizing additive compound is present in an amount from about 50 to about 2000 parts per million by weight (wt-ppm).

14. The monomer composition according to claim 1, wherein the color stabilizing additive compound is added prior to administration of an esterification/transesterification catalyst.

* * * * *